(12) United States Patent
Thabeth et al.

(10) Patent No.: US 9,103,811 B2
(45) Date of Patent: Aug. 11, 2015

(54) EXPANDABLE ENCLOSURE FOR OIL-IN-WATER ANALYZERS

(75) Inventors: Khalid Thabeth, Newtownabbey (GB); Raymond Acheson, Carrickfergus (GB); John Tierney, Carrickfergus (GB)

(73) Assignee: Advanced Sensors Limited, Carrickfergus, Antrim, NIR (GB)

( * ) Notice: Subject to any disclaimer, the term of this patent is extended or adjusted under 35 U.S.C. 154(b) by 397 days.

(21) Appl. No.: 13/817,581

(22) PCT Filed: Aug. 19, 2011

(86) PCT No.: PCT/EP2011/064324
§ 371 (c)(1),
(2), (4) Date: Apr. 2, 2013

(87) PCT Pub. No.: WO2012/022809
PCT Pub. Date: Feb. 23, 2012

(65) Prior Publication Data
US 2014/0144215 A1   May 29, 2014

(30) Foreign Application Priority Data

Aug. 20, 2010  (GB) .................................. 1013960.8

(51) Int. Cl.
*G01N 33/20* (2006.01)
*G01N 33/18* (2006.01)
*G01N 33/28* (2006.01)
*G01N 21/85* (2006.01)
*G01N 21/15* (2006.01)

(52) U.S. Cl.
CPC ................ *G01N 33/18* (2013.01); *G01N 21/85* (2013.01); *G01N 33/1833* (2013.01); *G01N 33/2847* (2013.01); *G01N 2021/154* (2013.01)

(58) Field of Classification Search
None
See application file for complete search history.

(56) References Cited

U.S. PATENT DOCUMENTS

| 2,517,603 | A | * | 8/1950 | Silverman | .................. | 73/152.41 |
| 4,116,045 | A | | 9/1978 | Potter | | |
| 5,929,453 | A | * | 7/1999 | Andrews et al. | ........... | 250/461.1 |
| 5,986,208 | A | * | 11/1999 | Taylor et al. | ................ | 174/50.58 |
| 2007/0169957 | A1 | * | 7/2007 | Ashibe et al. | ............... | 174/125.1 |
| 2007/0180939 | A1 | * | 8/2007 | Sciulli et al. | ................. | 73/866.5 |

FOREIGN PATENT DOCUMENTS

| WO | WO 2007/096179 A1 | 8/2007 |
| WO | WO 2009/138849 A1 | 11/2009 |

* cited by examiner

*Primary Examiner* — Herzon E Williams
*Assistant Examiner* — Truong Phan
(74) *Attorney, Agent, or Firm* — Gunn Lee & Cave, P.C.

(57) ABSTRACT

An electronic equipment enclosure (10), especially for an oil-in-water analyzer. The enclosure has a metal body (22) including an expandable folded section (26) that expands in response to increased pressure within the enclosure thereby increasing the volume defined by the enclosure. The enclosure is capable of containing internal explosions and is suitable for use in hazardous environments where the electronic equipment can come into contact with explosive gases.

5 Claims, 4 Drawing Sheets

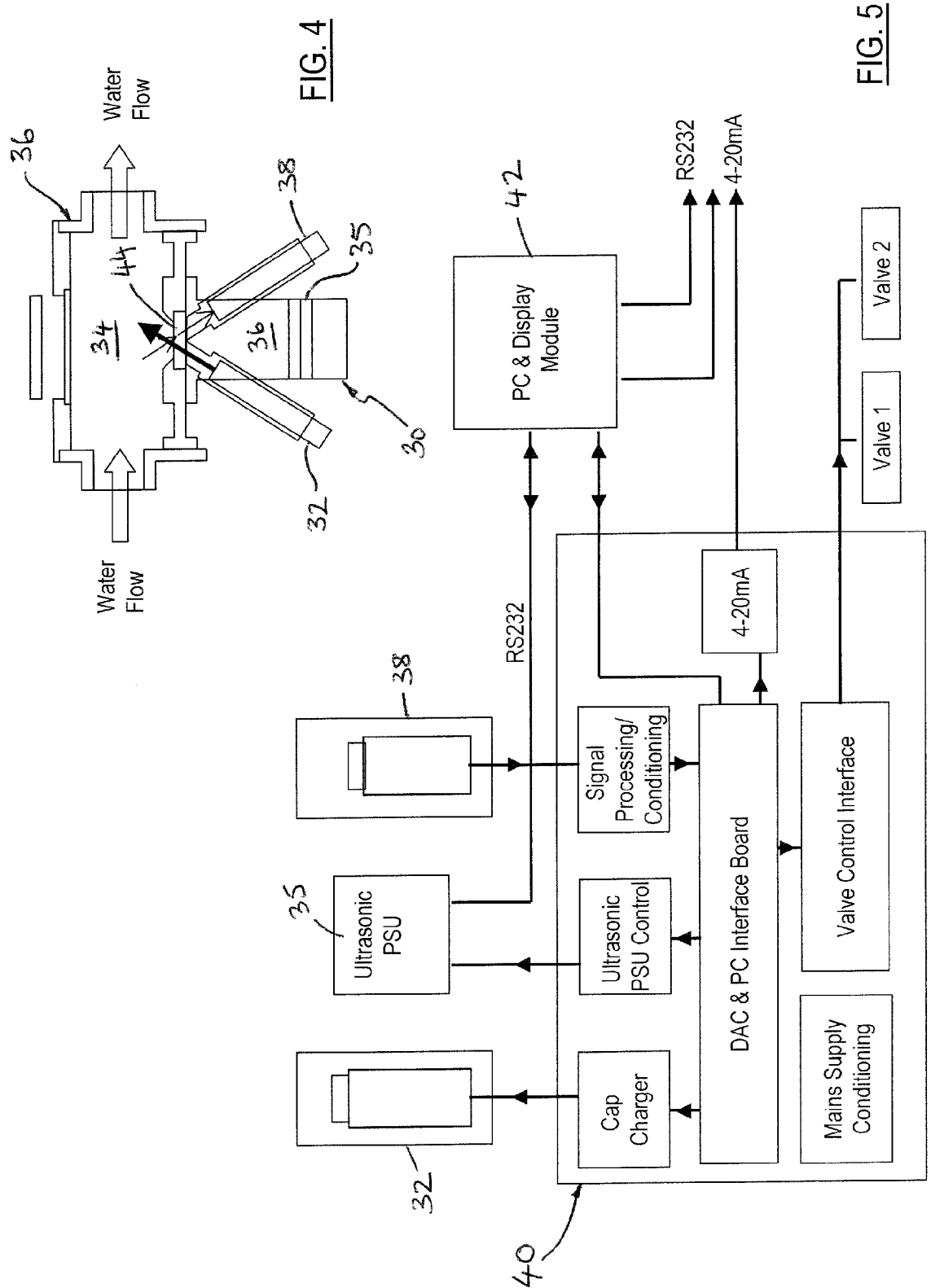

EXPANDABLE ENCLOSURE FOR OIL-IN-WATER ANALYZERS

FIELD OF THE INVENTION

The invention relates to enclosures, especially for oil-in-water analysers.

BACKGROUND TO THE INVENTION

Enclosures for oil-in-water (OIW) analysers undergo rigorous testing in order to achieve industry standard hazard approval ratings. To meet industry standards concerning the strength of the enclosure, a conventional approach is to select a wall thickness that provides the required strength. For example, for a stainless steel enclosure, a typical wall thickness is 12 mm.

A problem associated with enclosures for OIW analysers is that they are susceptible to explosions within the enclosure as a result of combustible material, especially gas, coming into contact with the electronics contained within the enclosure. Selecting the thickness of the walls of the enclosure so that it can withstand such explosions is the conventional solution.

Relatively thick-walled enclosures are considered undesirable, as they are heavy and expensive. It would be desirable therefore to provide an improved enclosure for oil-in-water analysers.

SUMMARY OF THE INVENTION

Accordingly, from a first aspect, the invention provides an enclosure, especially but not exclusively for an oil-in-water (OIW) analyser, the enclosure having a body provided with at least one expandable folded section. Advantageously, said at least one expandable folded section is arranged to expand in response to increased pressure within the enclosure thereby increasing the volume defined by the enclosure. Advantageously, at least said at least one expandable folded section is formed from metal. The enclosure is capable of containing internal explosions.

Preferably, said at least one folded section is formed by at least two substantially parallel folds running around the periphery of the body, typically around the entire periphery. More preferably, said at least one folded section comprises at least three folds to define a channel running around the periphery of the enclosure. The channel may be substantially V-shaped or substantially U-shaped, in which case at least four substantially parallel folds are required.

In the preferred embodiment, said at least one folded section comprises a recessed annular channel running around the entire periphery of the body. Optionally, said at least one folded section is defined by a first section in which the width of the enclosure decreases (preferably gradually), followed by a second section, in which the width of the enclosure remains substantially constant, and a third section in which the width of the enclosure increases, preferably gradually and more preferably to substantially the same width as the width of the enclosure on the opposite side of the folded section. Each of said first, second and third sections is separated by respective parallel folds formed in the body. One or both of the first and third sections may contain one or more additional substantially parallel folds such that it has a non-linear profile.

In the preferred embodiment, the enclosure has a single folded section. Alternatively, the enclosure may be provided with more than one folded section, each folded section typically being substantially parallel with the other(s).

Conveniently, the body, or at least said at least one folded section, is formed from a sheet of metal, preferably stainless steel.

In typical embodiments, the enclosure houses an OIW analyser or other electronic equipment. The OIW analyser typically comprises a sensor head, a user interface and electronic circuitry (usually including a programmable processor with associated circuitry for communicating with the sensor head and the user interface). The user interface usually includes a display screen. The electronic circuitry and user interface are typically located inside the enclosure. The sensor head may be fully or partly located in the enclosure so long as it may be suitably exposed to a sample that requires analysis. Alternatively, the sensor head may be located outside of the enclosure and connected to the internal components of the analyser by any suitable means.

From a second aspect the invention provides an oil-in-water analysing apparatus comprising an enclosure of the first aspect of the invention with at least some components, especially electronic components of an OIW analyser housed within the enclosure.

The term oil-in-water analyzer as used herein is intended to embrace analyzers that are capable of detecting oil but also any other contaminants or substances that may be present. It will be understood that OIW analyzers may be configured to detect contaminants (especially those that are suspended and/or in particulate or discrete form) in a liquid, and are not limited to detecting oil in water. More generally, the invention may adapted for use with analyzers that detect substances in a liquid.

From a third aspect, the invention provides an electronic equipment enclosure, the enclosure having a body provided with at least one expandable folded section. Advantageously, said at least one expandable folded section is arranged to expand in response to increased pressure within the enclosure thereby increasing the volume defined by the enclosure.

From a fourth aspect, the invention provides an enclosure for containing explosions within itself, the enclosure having a body provided with at least one expandable folded section, said at least one expandable folded section being arranged to expand in response to increased pressure within the enclosure thereby increasing the volume defined by the enclosure, and wherein said at least one expandable folded section is formed from metal.

Further advantageous aspects of the invention will become apparent for those ordinarily skilled on the art upon review of the following disclosure of a specific embodiment and with reference to the accompanying drawings.

BRIEF DESCRIPTION OF THE DRAWINGS

An embodiment of the invention is now described by way of example and with reference to the accompanying drawings in which:

FIG. 4 shows an example of an optical head coupled to a sample chamber; and

FIG. 5 is a schematic view of a typical oil-in-water analyzer.

DETAILED DESCRIPTION OF THE DRAWINGS

Figure 1:
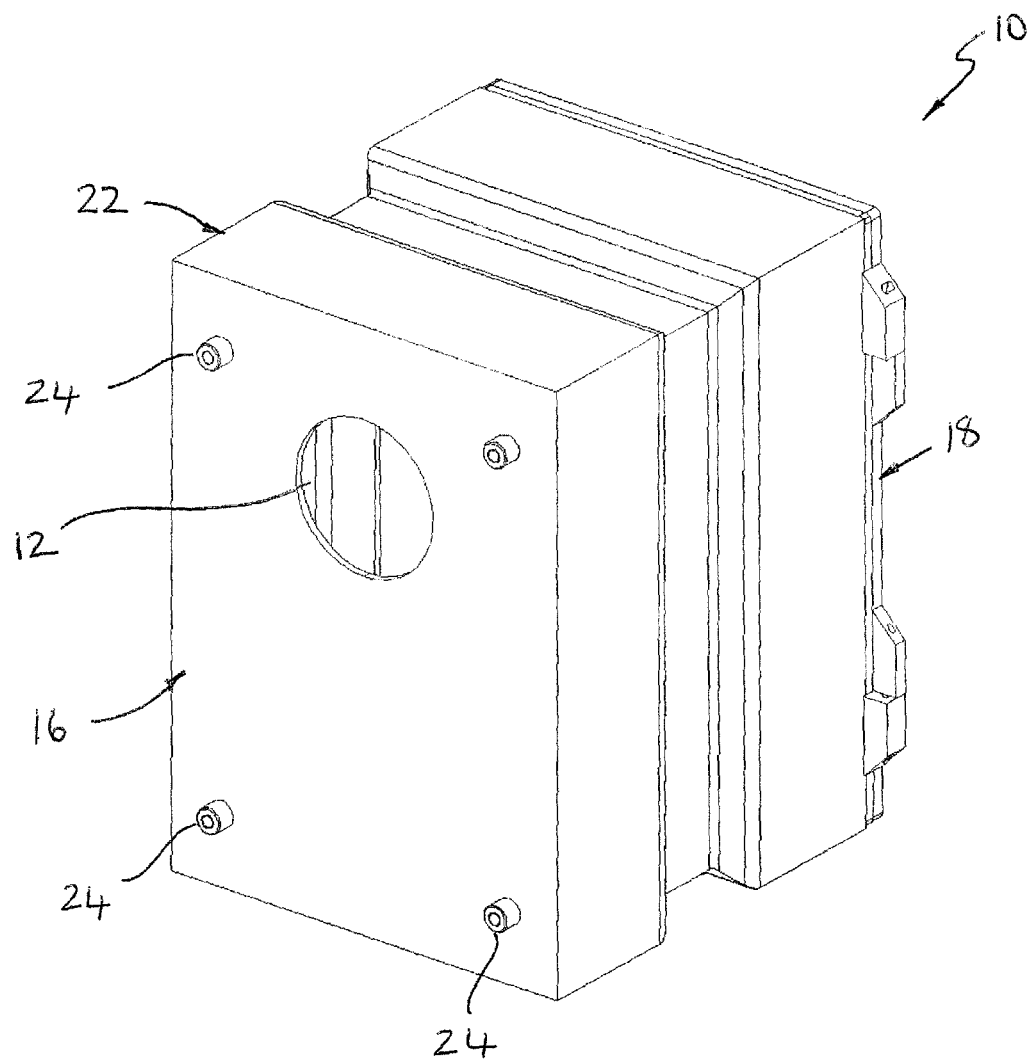
FIG. 1 is a perspective front view of an enclosure embodying the invention.
Figure 2:
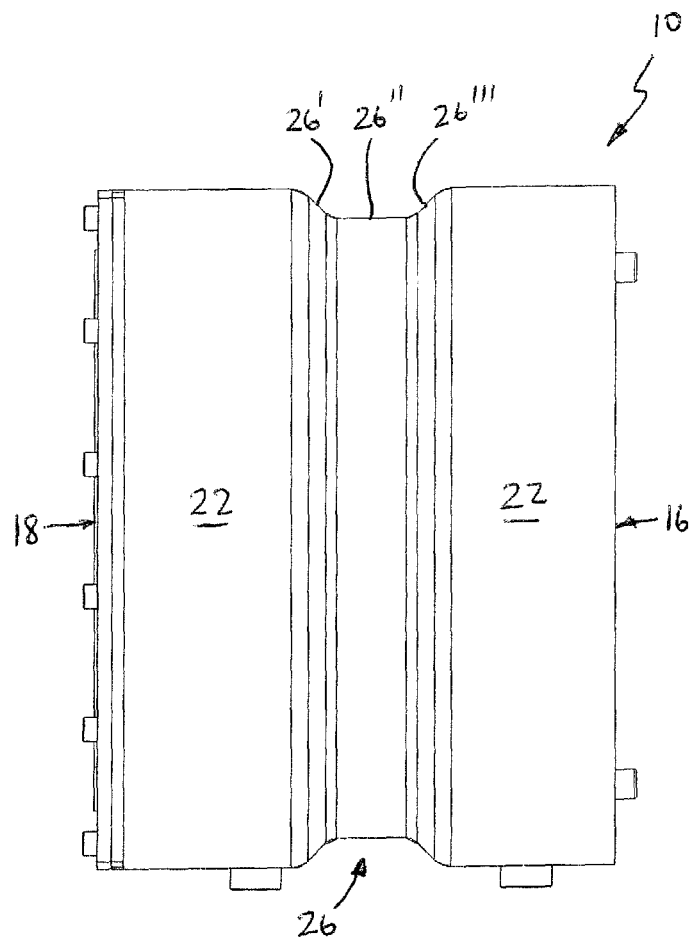
FIG. 2 is a side view of the enclosure of FIG. 1.
Figure 3:
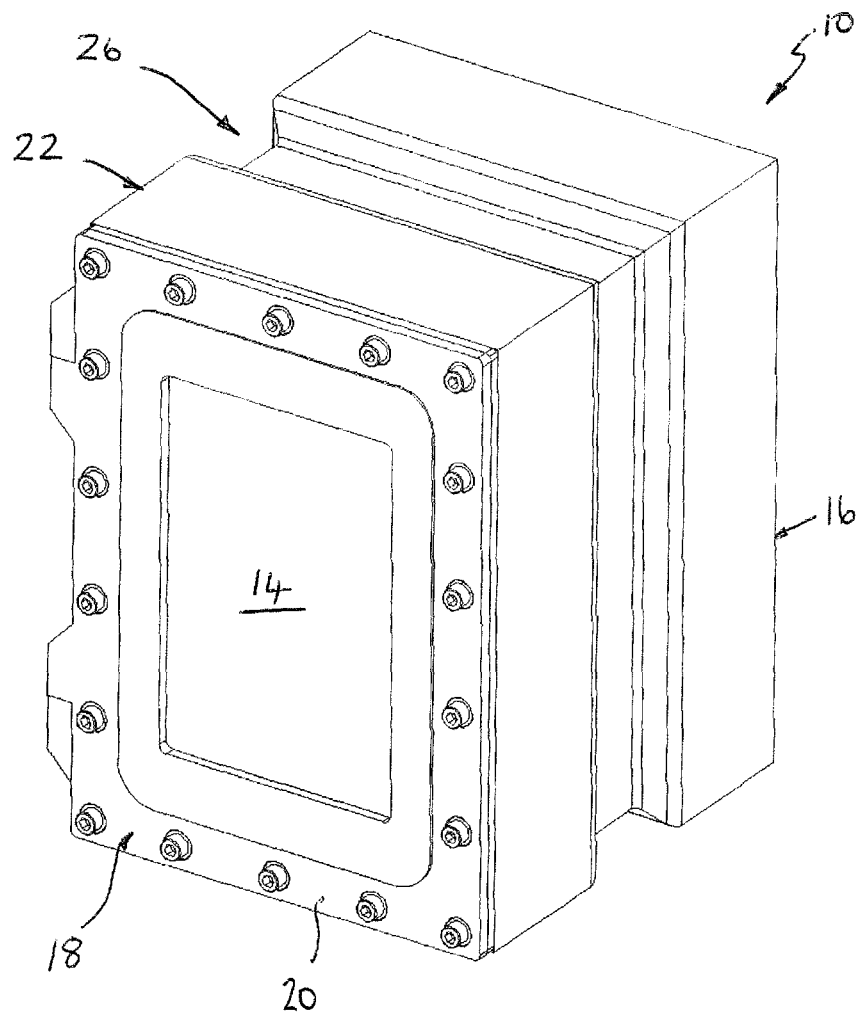
FIG. 3 is a perspective rear view of the enclosure view of FIG. 1.

Referring now to the drawings, there is shown, generally indicated as 10, an enclosure embodying one aspect of the present the invention. The enclosure 10 is particularly intended for accommodating some or all of the components of a liquid analyzer, especially an oil-in-water (OIW) analyser. It is alternatively suitable for use as a housing for other electronic equipment, especially equipment that may come into contact with explosive gases during use.

FIGS. 4 and 5 illustrate a typical OIW analyzer. Referring first to FIG. 4, the OIW analyser typically comprises a sensing head 30 that is capable of detecting the presence of oil, and/or other substances, in water. The sensor head 30 is commonly an optical sensor head, comprising an illumination source 32 (for example one or more lasers and/or LEDs) arranged to illuminate a water sample 34, typically contained in a sample chamber 36 (which may comprise a pipe section), and an optical receiver 38 arranged to receive light from the illuminated sample and to produce a corresponding electrical output. The head 30 may also include an ultrasonic vibration device 35 for imparting ultrasonic vibrations to the body 37 of the sensing head 39.

Referring to FIG. 5, the OIW analyser may further include electronic circuitry 40 for controlling the operation of the sensor head 30 and for processing signals produced by the sensor head. In the illustrated example, the circuitry 40 includes a charger for the light source, an ultrasonic controller, a signal processing unit, an interface unit, a mains supply conditioning unit and a valve controller (for controlling values that allow water samples into and out of the chamber 36). The analyser may also comprise a programmable processor 42, typically a microprocessor, programmed to control the sensor head and analyse signals produced by the sensor head. The analyser usually also includes a user interface including a display screen. It will be understood that the electronic circuitry may differ from embodiment to embodiment.

In typical embodiments, the electronic circuitry 40 is located inside the enclosure 10. The processor 42 may also be located within the enclosure. Alternatively, the processor 42, especially where the processor 42 comprises a PC, may be located outside of the enclosure and be in communication with the circuitry 40 by a wired and/or wireless link. In some cases, there may be a processor inside the enclosure and a processor outside of the enclosure. In any case, a video display screen is typically located inside the enclosure 10, which is connected to the processor inside and/or outside (as applicable) of the enclosure 10 (and/or optionally to the circuitry 40) for displaying information concerning the operation of the analyzer.

In some embodiments, the enclosure 10 is adapted to be coupled, e.g. mechanically connected, to the sample chamber 36 (for example in a manner the same or similar to that shown in FIG. 4), in which case there is typically a window 44 at the interface between the enclosure 10 and the chamber 36. In such embodiments, the sensing head 30 is located within the enclosure 10 and is positioned to send and receive signals through the window 44 during use. In alternative embodiments (not illustrated), the sensing head is incorporated into a probe outside of the enclosure 10, the probe being in communication with the circuitry 40 by any suitable wired or wireless link. The probe may be brought into contact with a water sample, e.g. by inserting it into a sample chamber or any other vessel or pipe.

In the illustrated embodiment, the enclosure 10 includes an aperture 12 for exposing the sensor head 30. When the enclosure 10 is coupled to a sample chamber, or the like (e.g. a pipe section), the aperture 12 is aligned with the window 44. The window 44 may be incorporated into the aperture 12, or may be incorporated into the sample chamber. In alternative embodiments where the sensor head takes the form of a probe, the aperture is not required since the probe may be connected, e.g. for communication purposes, to the analyser components in the enclosure by means of a wired or wireless connection. The enclosure 10 may also include a window 14 for exposing the display screen and/or other user interface.

In typical embodiments, the aperture 12 is provided in a front end 16 of the enclosure 10 and the window 14 is provided in an oppositely disposed rear end 18. The enclosure 10 typically includes an access hatch 20, which may be opened to allow a user access to the analyser components, e.g. for the purposes of operation, setup and so on. In the illustrated embodiment, the hatch 20 takes the form of a hinged door provided at the rear end 18 of the enclosure 10.

The enclosure 10 has a body 22 extending between the front and rear ends 16, 18. The preferred enclosure 10 is substantially rectangular in longitudinal and transverse cross section. It will be seen from the drawings that, in the preferred embodiment, the front and rear end 16, 18 are substantially rectangular in shape, and the body 22 extending between them has a substantially rectangular transverse cross section. The longitudinal cross section of the body 22 is generally rectangular although, as is described in more detail hereinafter, includes at least one expandable fold.

The body 22 is provided with at least one expandable folded section 26. The folded section 26 is formed by at least two substantially parallel folds, or fold lines, running around the periphery of the body 22, preferably around the entire periphery. Preferably, the folded section 26 comprises at least three folds to define a notch or channel running around the periphery of the enclosure 10. The channel may be substantially V-shaped (not illustrated) or substantially U-shaped, in which case at least four substantially parallel folds are required.

In the preferred embodiment, the folded section 26 comprises a recessed channel running around the entire periphery of the body 22. Thus, the folded section 26 is annular and, in this example, runs transversely around the body 22 and is disposed between, and substantially parallel with, ends 16, 18 of the enclosure 10. The preferred folded section 26 is defined by a first section 26' in which the width of the enclosure decreases (preferably gradually, i.e. the section 26' is sloped), followed by a second section 26" in which the width of the enclosure remains substantially constant, and a third section 26'" in which the width of the enclosure 10 increases, preferably gradually and more preferably to substantially the same width as the width of the enclosure on the opposite side of the folded section 26. Each section 26', 26", 26'" is separated by respective parallel folds formed in the body 22. One or both of the sloped sections 26', 26'" may contain one or more additional substantially parallel folds such that it has a non-linear profile.

In the preferred embodiment, the enclosure 10 has a single folded section 26. Alternatively, enclosure 10 may be provided with more than one folded section. Each folded section may be as described above, although the folded sections need not necessarily be the same. Each folded section may be said to comprise a single corrugation.

Typically, body 22, or at least the folded section 26, is formed from metal, usually a sheet of metal, preferably stainless steel, which is pre-folded to define the folded section 26 before being incorporated into the enclosure 10. The entire body 22 may be formed from a single folded metal sheet. Alternatively, the folded section 26 may be formed from a single metal sheet and then welded, or otherwise fixed, between further sections to form the body 22. The body 22 is connected to the ends 16, 18 by any suitable means, e.g. welding.

In use, the enclosure 10 may be mounted to structure, e.g. a pipe or chamber, that contains water (or other liquid) to be analysed. The enclosure 10 is mounted to the structure such that the sensor head is exposed to the sample. In the illustrated embodiment, the enclosure 10 may be mounted to the structure by its front end 16 by any suitable means (see for example threaded sockets 24 which allow the enclosure to be mounted to a compatibly equipped structure). Alternatively, the enclosure 10 may be adapted to be mounted in line between two structures, e.g. between two pipe sections. Alternatively still, the enclosure 10 may be portable, in which case the sensor head may take the form of a probe that is insertable into a water sample.

The enclosure 10 defines an enclosed space for receiving the relevant components of the OIW analyzer (or other items) which, in use, is closed to the external environment and may be substantially air-tight.

During use, in the event of an explosion inside the enclosure 10, the folded section 26 wholly or partly unfolds to enable the body 22 to expand in the longitudinal direction. This results in an appreciable drop in pressure within the enclosure 10 that allows the explosion to be contained. The folded section 26 also has the effect of increasing the strength of the enclosure 10 in comparison with enclosures with no folded sections. As a result, it is found that the enclosure 10, and in particular the body 22, can be made from a material with reduced thickness when compared to conventional enclosures. For example, in cases where the enclosure, and in particular the body 22, is formed from stainless steel, it is found that the body 22 may be approximately 6 mm thick for typical applications. This reduces the cost of the enclosure as well as making it lighter and therefore improving is portability.

Enclosures embodying the invention are capable of containing external explosions and, while enclosures embodying the present invention are particularly suited for oil-in-water analysers, it will be apparent that they may find other applications, especially relating to hazardous environments where gas may seep into the enclosure and cause an internal explosion.

The invention is not limited to the embodiment described herein which may be modified or varied without departing from the scope of the invention.

The invention claimed is:

1. An electronic equipment enclosure, the enclosure having a body provided with at least one expandable folded section, said at least one expandable folded section being arranged to expand in response to increased pressure within the enclosure thereby increasing the volume defined by the enclosure;

said at least one folded section is defined by a first section in which the width of the enclosure decreases towards a second section adjacent the first section, in which the width of the enclosure remains substantially constant, and a third section adjacent the second section, in which the width of the enclosure increases in a direction away from said second section, each of said first, second and third sections being separated by respective parallel folds formed in the body.

2. An enclosure as claimed in claim 1, wherein the width of the enclosure decreases gradually in said third section.

3. An enclosure as claimed in claim 1, wherein the width of the enclosure increases gradually in said third section.

4. An enclosure as claimed in claim 1 wherein the width of the enclosure increases in said third section to substantially the same width as the width of the enclosure on the opposite side of the folded section.

5. An enclosure as claimed in claim 1 wherein one or both of the first and third sections includes one or more additional substantially parallel folds such that it has a non-linear profile.

* * * * *